US00PP25157P2

(12) United States Plant Patent

Miyazaki et al.

(10) Patent No.: US PP25,157 P2

(45) Date of Patent: Dec. 9, 2014

(54) *VERBENA* PLANT NAMED 'SUNMARIROSTA'

(50) Latin Name: *Verbena hybrida*
Varietal Denomination: Sunmarirosta

(71) Applicants: Kiyoshi Miyazaki, Shiga (JP); Tomoya Misato, Shiga (JP)

(72) Inventors: Kiyoshi Miyazaki, Shiga (JP); Tomoya Misato, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 108 days.

(21) Appl. No.: 13/815,127

(22) Filed: Jan. 31, 2013

(51) Int. Cl.
*A01H 5/00* (2006.01)

(52) U.S. Cl.
USPC ..... Plt./308

(58) Field of Classification Search
USPC ..... Plt./308
See application file for complete search history.

*Primary Examiner* — Susan McCormick Ewoldt
(74) *Attorney, Agent, or Firm* — C. A. Whealy

(57) ABSTRACT

A new and distinct cultivar of *Verbena* plant named 'Sunmarirosta', characterized by its compact, semi-upright and mounding plant habit; vigorous growth habit; freely branching habit; early and freely flowering habit; long flowering period; light pink and red purple bi-colored flowers that are held above and beyond the foliar plane; and good garden performance.

1 Drawing Sheet

Botanical designation: *Verbena hybrida.*
Cultivar denomination: 'SUNMARIROSTA'.

BACKGROUND OF THE INVENTION

The present invention relates to a new and distinct cultivar of *Verbena* plant, botanically known as *Verbena hybrida*, and hereinafter referred to by the name 'Sunmarirosta'.

The new *Verbena* plant is a naturally-occurring branch mutation of a proprietary selection of *Verbena hybrida* identified as code number 1800, not patented. The new *Verbena* plant was discovered and selected by the Inventors on a single flowering plant of the patent selection in a controlled greenhouse environment in Higashiomi, Shiga, Japan in July, 2009.

Asexual reproduction of the new *Verbena* plant by terminal cuttings in a controlled environment in Higashiomi, Shiga, Japan since July, 2009 has shown that the unique features of this new *Verbena* plant are stable and reproduced true to type in successive generations.

SUMMARY OF THE INVENTION

Plants of the new *Verbena* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunmarirosta'. These characteristics in combination distinguish 'Sunmarirosta' as a new and distinct *Verbena* plant:

1. Compact, semi-upright and mounding plant habit.
2. Vigorous growth habit.
3. Freely branching habit.
4. Early and freely flowering habit.
5. Long flowering period.
6. Light pink and red purple bi-colored flowers that are held above and beyond the foliar plane.
7. Good garden performance.

Plants of the new *Verbena* can be compared to plants of the parent selection. Plants of the new *Verbena* differ primarily from plants of the parent selection in flower color as plants of the parent selection have solid red purple-colored flowers.

Plants of the new *Verbena* can be compared to plants of *Verbena* 'Sunmaricoaka', disclosed in U.S. Plant Pat. No. 22,849. In side-by-side comparisons conducted in Higashiomi, Shiga, Japan, plants of the new *Verbena* differed primarily from plants of 'Sunmaricoaka' in the following characteristics:

1. Plants of the new *Verbena* were broader than plants of 'Sunmaricoaka'.
2. Plants of the new *Verbena* had shorter internodes than plants of 'Sunmaricoaka'.
3. Plants of the new *Verbena* had lighter green-colored leaves than plants of 'Sunmaricoaka'.
4. Plants of the new *Verbena* were more freely flowering than plants of 'Sunmaricoaka'.
5. Plants of the new *Verbena* had smaller flowers with more narrower petals than plants of 'Sunmaricoaka'.
6. Plants of the new *Verbena* and 'Sunmaricoaka' differed in flower color as plants of 'Sunmaricoaka' had red-colored flowers.
7. Plants of the new *Verbena* had shorter peduncles than plants of 'Sunmaricoaka'.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the colors of the new *Verbena.*

The photograph at the top of the sheet comprises a side perspective view of a typical flowering plant of 'Sunmarirosta' grown in a container.

The photograph at the bottom of the sheet is a close-up view of a typical flowering plant of 'Sunmarirosta'.

DETAILED BOTANICAL DESCRIPTION

The aforementioned photographs and following observations and measurements describe plants grown during the summer in 15-cm containers in an outdoor nursery in Higashiomi, Shiga, Japan and under cultural practices typical of commercial production. During the production of the plants, day temperatures averaged 23° C. and night temperatures averaged 13° C. Plants were four months old when the photographs and description were taken. In the following description color references are made to The Royal Horticultural Society Colour Chart, 2007 Edition, except where general terms of ordinary dictionary significance are used.

Botanical classification: *Verbena hybrida* 'Sunmarirosta'.

Parentage: Naturally-occurring branch mutation of a proprietary selection of *Verbena hybrida* identified as code number 1800, not patented.

Propagation:

*Type*.—By terminal cuttings.

*Time to initiate roots*.—About 10 to 14 days at 20° C. to 25° C.

*Time to produce a rooted young plant*.—About four weeks at 20° C. to 25° C.

*Root description*.—Fibrous; white in color.

*Rooting habit*.—Freely branching.

Plant description:

*Plant and growth habit*.—Compact, semi-upright and mounding growth habit; freely branching habit with numerous lateral branches developing per plant; pinching enhances lateral branch development; vigorous growth habit.

*Plant height*.—About 22 cm.

*Plant diameter*.—About 71.5 cm.

Lateral branch description:

*Length*.—About 35 cm.

*Diameter*.—About 2.6 mm.

*Internode length*.—About 2.7 cm.

*Strength*.—Strong.

*Aspect*.—Upright to outwardly.

*Texture*.—Densely pubescent.

*Color*.—Close to 144B tinged with close to 165A.

Foliage description:

*Arrangement*.—Opposite, simple.

*Length*.—About 4.3 cm.

*Width*.—About 3 cm.

*Shape*.—Ovate.

*Apex*.—Broadly acute.

*Base*.—Truncate.

*Margin*.—Crenate.

*Texture, upper and lower surfaces*.—Pubescent; coarse.

*Venation pattern*.—Pinnate; reticulate.

*Color*.—Developing leaves, upper and lower surfaces: Close to 143A. Fully expanded leaves, upper surface: Close to 137C; venation, close to 144D. Fully expanded leaves, lower surface: Close to 137D; venation, close to 144D.

*Petiole*.—Length: About 4.6 cm. Diameter: About 0.9 mm. Texture, upper and lower surfaces: Pubescent. Color, upper and lower surfaces: Close to 144D.

Flower description:

*Flower arrangement and flowering habit*.—Single salverform flowers arranged in hemispherical terminal racemes; flowers face mostly upright; freely flowering habit with about 24 flowers per inflorescence and about 35 inflorescences developing per plant.

*Natural flowering season*.—Early flowering habit, plants begin flowering about four weeks after planting; long flowering period, plants flower continuously from spring to late autumn in Japan.

*Flower longevity*.—Flowers last about one week on the plant; flowers not persistent.

*Fragrance*.—None detected.

*Inflorescence height*.—About 4.7 cm.

*Inflorescence diameter*.—About 6.1 cm.

*Flowers*.—Diameter: About 1.9 cm. Depth (height): About 2.6 cm. Throat diameter: About 1.2 mm. Tube length: About 2 cm. Tube diameter, mid-section: About 1.8 mm.

*Flower buds*.—Length: About 1.4 cm. Diameter: About 3.1 mm. Shape: Clavate. Color: Close to 60B and 49B.

*Corolla*.—Arrangement: Single whorl of five fused petals. Petal length: About 10.2 mm. Petal width: About 7.6 mm. Petal lobe shape: Narrowly obcordate. Petal lobe apex: Emarginate. Petal margin: Entire. Petal texture, upper and lower surfaces: Smooth, glabrous. Tube texture: Smooth, glabrous. Color: Petal, when opening, upper surface: Close to 58D; thick longitudinal lines, close to N57A. Petal, when opening, lower surface: Close to 68D; thick longitudinal lines, close to 61C. Petal, fully opened, upper surface: Close to 49C; thick longitudinal lines, close to N57B; towards the base, close to NN155A; with development, main colors become closer to 69D and 63C. Petal, fully opened, lower surface: Close to 56D; thick longitudinal lines, close to 64C. Throat: Close to 149D. Tube: Close to 149D.

*Calyx*.—Arrangement: One single narrow calyx tube per flower with five fused sepals. Sepal length: About 1 cm. Sepal width: About 1 mm. Sepal shape: Lanceolate. Sepal apex: Acute. Sepal margin: Entire. Sepal texture, upper and lower surfaces: Smooth, glabrous. Sepal color, immature, upper and lower surfaces: Close to 144C. Sepal color, mature, upper and lower surfaces: Close to 144C.

*Peduncles*.—Length: About 1.7 cm. Diameter: About 1.5 mm. Strength: Strong. Aspect: Mostly upright. Texture: Pubescent. Color: Close to 144A.

*Reproductive organs*.—Stamens: Quantity per flower: Four. Anther shape: Ellipsoidal. Anther size: About 0.5 mm by 1 mm. Anther color: Close to N144D. Pollen amount: Scarce. Pollen color: Close to N144D. Pistils: Quantity per flower: One. Pistil length: About 1.6 cm. Stigma shape: Bi-parted. Stigma color: Close to 144B. Style color: Close to 144D. Ovary color: Close to 144B. Fruits and seeds: Fruit and seed development have not been observed on plants of the new *Verbena*.

Garden performance: Plants of the new *Verbena* have been observed to have good garden performance and to tolerate wind, rain and temperatures ranging from about 0° C. to about 35° C.

Pathogen & pest resistance: Plants of the new *Verbena* have not been observed to be resistant to pathogens and pests common to *Verbena* plants.

It is claimed:

1. A new and distinct *Verbena* plant named 'Sunmarirosta' as illustrated and described.

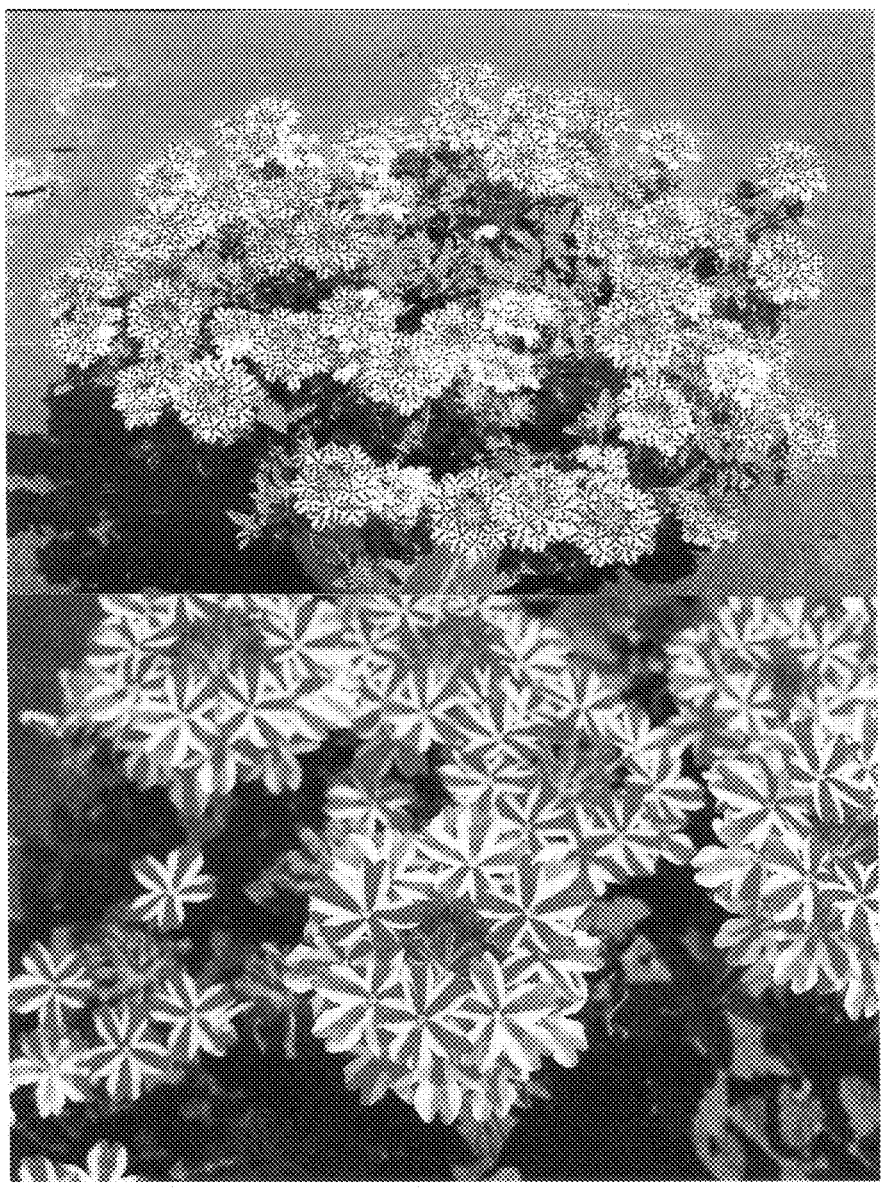

* * * * *